| United States Patent [19] | [11] Patent Number: 4,976,950 |
| Simon et al. | [45] Date of Patent: * Dec. 11, 1990 |

[54] BONE MARROW SUPPRESSING AGENTS

[75] Inventors: Jaime Simon, Angleton; Joseph R. Garlich, Lake Jackson; David A. Wilson, Richwood; Kenneth McMillan, Richwood, all of Tex.

[73] Assignee: The Dow Chemical Company, Midland, Mich.

[*] Notice: The portion of the term of this patent subsequent to Nov. 21, 2006 has been disclaimed.

[21] Appl. No.: 435,096

[22] Filed: Nov. 13, 1989

Related U.S. Application Data

[63] Continuation-in-part of Ser. No. 284,875, Dec. 19, 1988, Pat. No. 4,882,142.

[51] Int. Cl.$^5$ ............................ A61K 43/00; C07F 5/00
[52] U.S. Cl. ..................................... 424/1.1; 534/10; 252/625
[58] Field of Search ........................... 424/1.1; 534/10; 252/625, 645

[56] References Cited

U.S. PATENT DOCUMENTS

| 4,508,625 | 4/1985 | Graham | 210/695 |
| 4,678,667 | 7/1987 | Meares et al. | 424/85 |
| 4,853,209 | 8/1989 | Kaplan et al. | 424/1.1 |
| 4,882,142 | 11/1989 | Simon et al. | 424/1.1 |
| 4,898,724 | 2/1990 | Simon et al. | 424/1.1 |

FOREIGN PATENT DOCUMENTS 164843 12/1985 European Pat. Off. .
291605 10/1987 European Pat. Off. .

OTHER PUBLICATIONS

Keeling, A. A. et al., "A Bone Seeking Radiotherapeutic Agent," *Journal Nucl Medicine*, vol. 30, No. 5, May 1989.

*Primary Examiner*—John S. Maples

[57] ABSTRACT

The invention concerns a method for suppressing bone marrow which comprises administering to a mammal at least one bone marrow suppressing complex of a radionuclide selected from the group consisting of Samarium-153, Gadolinium-159, Holmium-166 and Yttrium-90 and at least one macrocyclic aminophosphonic acid ligand containing the 1,4,7,10-tetraazacyclododecane moiety, or a physiologically acceptable salt thereof. Suitable compositions for use in this method are also provided.

21 Claims, No Drawings

BONE MARROW SUPPRESSING AGENTS

CROSS-REFERENCE TO RELATED APPLICATION

This application is a continuation-in-part of U.S. Ser. No. 284,875, filed Dec. 19, 1988, now U.S. Pat. No. 4,882,142 issued Nov. 21, 1989.

BACKGROUND OF THE INVENTION

This invention pertains to a method of treating cancer and genetic diseases, particularly for the suppression or eradication of bone marrow, and to compositions having as their active ingredient a radionuclide complexed with a macrocyclic aminophosphonic acid.

The use of agents which cause partial or total suppression or eradication of the bone marrow has become an accepted part of some procedures used to treat patients with cancers such as leukemias, lymphomas, myelomas and Hodgkin's disease as well as in the treatment of patients suffering from genetic disorders such as sickle cell anemia and thalassemia.

For example, in the treatment of patients having acute lymphoblastic leukemia and acute nonlymphoblastic leukemia, it is sometimes beneficial to employ a therapy regimen which combines chemotherapy using drugs, such as cyclophosphamide, bischloroethyl nitrosourea, cytosine arabinoside, 6-thioguanine and the like, and total body irradiation, followed by bone marrow transplantation.

In situations where the patient is suffering from a genetic disability such as thalassemia or sickle cell anemia, bone marrow transplantation may offer the possibility of a cure. In thalassemia, the afflicted individual has a genetic disorder causing the production of an abnormal hemoglobin and is only able to survive by repeated blood transfusions. Nonetheless, children afflicted with thalassemia major rarely survive to adulthood. In sickle cell anemia, the individual produces an abnormal hemoglobin (i.e., hemoglobin S). The individual homozygous for hemoglobin S has red blood cells that assume a sickle shape at ordinary oxygen tensions. These sickled red blood cells encounter mechanical difficulties in moving through small blood vessels which can lead to thromboses and tissue anoxia.

The use of radionuclides for bone marrow suppression with a phosphonic acid ligand is discussed in published European patent application 291,605 where the use of Sm-153, Gd-159, or Ho-166 complexed with a ligand selected from ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), or tris(2-aminoethyl)aminehexamethylenephosphonic acid (TTHMP) is disclosed.

Bone marrow transplantation offers the possibility of eradicating the afflicted individual's defective bone marrow and replacing it with a normal, nonpathogenic, bone marrow. If the abnormal bone marrow of an individual suffering from sickle cell anemia or thalassemia can be eradicated and then replaced with a bone marrow which takes and is reproduced and capable of producing normal hemoglobin, the individual may be cured.

For those situations where bone marrow transplantation can aid in therapy or cure, it would be desirable to have a means of selectively suppressing the bone marrow independent of or with limited total body irradiation.

The present invention is directed to a method for the suppression of bone marrow and to a composition for use in the method. The method comprises administering to a mammal in need of such treatment a bone marrow suppressing amount of at least one composition comprised of a radionuclide complexed with a macrocyclic aminophosphonic acid containing 1,4,7,10-tetraazacyclododecane as the macrocyclic moiety. The method of bone marrow suppression described herein may be used in combination with chemotherapeutic drugs and/or external radiation.

The present invention has significant benefits in that it permits selective bone marrow suppression, that is, the bone marrow can be suppressed with only minimal damage to non-target soft tissues, for example, liver and kidney. Selective bone marrow suppression offers the opportunity to pursue particular treatment regimens which would otherwise be unavailable due to the concerns of excessive non-target soft tissue damage, for example, when total body irradiation is the sole or primary means of obtaining bone marrow suppression. Using the present invention for obtaining bone marrow suppression reduces the risk to the patient since the damage to non-target soft tissue is significantly reduced thereby promoting the general health of the patient and enhancing the prospect of the patient's recovery.

SUMMARY OF THE INVENTION

The invention concerns a method for suppressing bone marrow which comprises administering a composition to a mammal in need of such treatment a bone marrow suppressing amount of at least one radionuclide complexed with at least one macrocyclic aminophosphonic acid containing 1,4,7,10-tetraazacyclododecane as the macrocyclic moiety and wherein the phosphonic acid functionality is attached to the nitrogen of the macrocyclic polyamine through an alkylene group. In particular, the present invention is directed to a method for suppressing bone marrow which comprises administering to a mammal in need of such treatment a bone marrow suppressing amount of at least one bone marrow suppressing composition wherein said composition is comprised of at least one radionuclide selected from the group consisting of Samarium-153 (Sm-153), Gadolinium-159 (Gd-159), Holmium-166 (Ho-166), and Yttrium-90 (Y-90) complexed with at least one macrocyclic aminophosphonic acid ligand containing a 1,4,7,10-tetraazacyclododecane moiety as the macrocyclic moiety, or a physiologically acceptable salt thereof. The preferred macrocyclic aminophosphonic acid moiety is 1,4,7,10-tetraazacyclododecanetetramethylenephosphonic acid (DOTMP). The present invention includes the use of the bone marrow suppressing method and composition in combination with other drugs and/or radiation sources.

In addition the present invention also includes formulations having at least one of the radionuclide(s) complexed with at least one of the macrocyclic aminophosphonic acids of the invention and a pharmaceutically acceptable carrier, excipient or vehicle therefor. The methods for preparing such formulations are well known. The formulations are sterile and may be in the form of a suspension, injectable solution or other suitable pharmaceutically acceptable formulations. Physiologically acceptable suspending media, with or without adjuvants, may be used.

The present invention contemplates the use of one or more other agents or treatments which assist in obtaining bone marrow suppression when used in conjunction with the bone marrow suppressing radionuclide compositions described herein.

DETAILED DESCRIPTION OF THE INVENTION

The present invention is directed to a method for the suppression of bone marrow which comprises administering to a mammal in need of such treatment a bone marrow suppressing amount of at least one macrocyclic aminophosphonic acid-radionuclide composition. The present invention has significant benefits in that it permits selective bone marrow suppression (the bone marrow can be suppressed with only minimal damage to non-target soft tissues, for example, liver) without the need for large amounts of excess chelant. As will be more fully discussed later herein, the properties of the radionuclide, and of the radionuclide-macrocyclic aminophosphonic acid complex are important considerations in determining which radionuclide composition should be employed for any particular treatment.

It is important that the half-life of the radionuclide be sufficiently long to allow for its localization in the bone tissue while it still retains sufficient radioactivity to obtain bone marrow suppression. Generally it is preferred to use a radionuclide complex which results in rapid biolocalization of the radionuclide in the bone tissue so as to achieve bone marrow irradiation quickly. It is also beneficial to use a radionuclide having a relatively short half-life so that after bone marrow irradiation is achieved, it is possible to proceed with bone marrow transplantation as soon as possible in order to enhance the prospects of bone marrow engraftment and patient recovery. For example, certain radionuclides such as Sr-89 have been demonstrated, when selectively deposited in bone, to suppress bone marrow [see, for example, Y. Shibata et al., *J. Leukocyte Biol.* 38(6), 659-669 (December 1985)]. However, this compound is not clinically useful since the long half-life of Sr-89 (50 days) prevents transplantation of the new marrow for an unacceptable time. In order to increase the chance of the patient's recovery, it may be beneficial to employ materials, such as granulocyte-macrophage colony stimulating factor, which stimulate or enhance the regeneration of the bone marrow. Radionuclides useful in the method and compositions of this invention are Sm-153, Gd-159, Ho-166, and Y-90, especially preferred is Ho-166.

The radionuclide compositions employed in the method of the present invention are capable of delivering a significant portion of the radioactivity present in the composition to bone tissue rather than to non-target soft tissues. Therefore for those disease states where the treatment regimen requires bone marrow suppression, the present invention is particularly advantageous since it provides a means of achieving selective reduction in the hemopoietic stem cell population without having to resort to total body irradiation, thus resulting in minimal damage to non-target soft tissues. Furthermore, because there is a reduction in the radiation dose delivered to non-target tissues (as compared to the use of total body irradiation), the present invention offers the opportunity to use the same or increased chemotherapeutic dosages. In addition, if it is desirable to employ total body irradiation in conjunction with the bone marrow suppression method described herein, for example, in the treatment of leukemia, it may be possible to reduce the radiation dosage used for the total body irradiation and still obtain the same or higher level of reduction of leukemic cells.

The respective radionuclides can be produced in several ways. In a nuclear reactor, a nuclide is bombarded with neutrons to obtain a nuclide with additional neutrons in its nucleus.

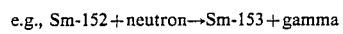

e.g., Sm-152+neutron→Sm-153+gamma

Typically the desired radionuclide can be prepared by irradiating an appropriate target, such as the metal oxide. Another method of obtaining radionuclides is by bombarding nuclides with particles in a linear accelerator or cyclotron. Yet another way of obtaining radionuclides is to isolate them from fission product mixtures. The method of obtaining the radionuclide is not critical.

Aminophosphonic acids can be prepared by a number of known synthetic techniques. Of particular importance is the reaction of a compound containing at least one reactive amine hydrogen with a carbonyl compound (aldehyde or ketone) and phosphorous acid or appropriate derivative thereof. The amine precursor (1,4,7,10-tetraazacyclododecane) employed in making the macrocyclic aminophosphonic acids is a commercially available material. The preparation of the macrocyclic aminophosphonic ligand of this invention can also be found in our copending application U.S. application Ser. No. 84,876, filed Dec. 19, 1988, (Attorney's docket C-2,813D) by Simon et al., the disclosure of which is hereby incorporated by reference.

The radionuclide and ligand may be combined under any conditions which allow the two to form a complex. Generally, mixing in water at a controlled pH (the choice of pH is dependent upon the choice of ligand and radio-nuclide) is all that is required. The complex formed is by a chemical bond and results in a relatively stable radionuclide composition, e.g. stable to the disassociation of the radionuclide from the ligand. The preferred bone marrow suppressing radionuclide composition utilizes Ho-166 with DOTMP.

For the purpose of convenience, the radionuclide-macrocyclic aminophosphonic acid compositions will frequently be referred to as "radionuclide compositions" and the macrocyclic aminophosphonic acid derivative referred to as the "ligand" or "chelant".

As used herein, the term "mammal" means a warm blooded mammal, including humans, and is meant to encompass mammals in need of bone marrow suppression, especially humans: thus in some instances the term "patient" is alternatively used for mammal.

The term "bone marrow suppression" refers to a partial or total eradication of the bone marrow, in particular a temporary or permanent reduction of the hemopoietic stem cell population.

For the purpose of the present invention, bone marrow suppressing radionuclide compositions described herein and physiologically acceptable salts thereof are considered equivalent. Physiologically acceptable salts refer to the acid addition salts of those bases which will form a salt with at least one acid group of the ligand or ligands employed and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Physiologically acceptable salts may be prepared by treating the macrocyclic aminophosphonic acid with an appropriate base.

The formulations of the present invention are in the solid or liquid form containing the active radionuclide complexed with the ligand. These formulations may be in kit form such that the two components are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt may be greater than the free acid. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50% of the organic solvent by volume.

Injectable suspensions as compositions of the present invention require a liquid suspending medium, with or without adjuvants, as a carrier. The suspending medium can be, for example, aqueous polyvinylpyrrolidone, inert oils such as vegetable oils or highly refined mineral oils, or aqueous carboxymethlycellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances which effect the hydrophibicity, density, and surface tension of the liquid suspension medium can assist in making injectable suspensions in individual cases. For example, silcone antifoams, sorbitol, and sugars are all useful suspending agents.

Radionuclide compositions suitable for use in the present invention must have particular properties to be suitable bone marrow suppressing agents. The properties of the particular radionuclide and the particular ligand are important: however, the properties of the combinations of the ligand and radionuclide (that is, the radionuclide compositions) are particularly important. The radionuclide must be taken up preferentially by bone so that it is possible to deliver a bone marrow suppressing dose of radiation to the bone marrow. The radionuclide also should be cleared rapidly from the blood.

The macrocyclic aminophosphonic acid complexes when administered at approximately a ligand to metal molar ratio of 1:1 to 2:1 give biodistributions that are consistent with excellent skeletal agents. By contrast, other aminophosphonic acid complexes result in substantial localization in soft tissue (e.g. liver) if large excess amounts of ligand are not used. Excess ligand is undesirable since uncomplexed ligand may be toxic to the patient or may result in cardiac arrest or hypocalcemic convulsions. In addition, the macrocyclic aminophosphonic acid ligands are useful when large amounts of metal are required (i.e. for metals that have a low specific activity). In this case, the macrocyclic aminophosphonic acid ligands have the ability to deposit larger amounts of activity in the bone than is possible when using noncyclic aminophosphonic acid ligands.

The "bone marrow suppressing amount" of radionuclide composition to be administered to achieve bone marrow suppression will vary according to factors such as the age, weight and health of the patient, the disease state being treated, the treatment regimen selected as well as the nature of the particular radionuclide composition to be administered. For example, less activity will be needed for radionuclides with longer half lives. The energy of the emissions will also be a factor in determining the amount of activity necessary. The preferred range of activity is from about 18 megabecquerels to 1850 megabecquerels per kilogram of body weight of animal to be treated: more preferred is from about 185 megabecquerels to 1850 megabecquerels per kilogram of body weight.

The effective amount used to obtain bone marrow suppression will typically be administered, generally by administration into the bloodstream, in a single dose. The amounts to be administered to achieve bone marrow suppression are readily determined by one skilled in the art employing standard procedures.

As noted previously, the amount of the radionuclide composition used will depend, in part, on the treatment regimen which is selected. For example, in the treatment of a patient having leukemia, the use of the radionuclide compositions described herein can reduce the leukemic cell population in the bone marrow: however, it will usually be necessary to use one or more chemotherapeutic agents, such as dimethyl busulfan and/or cyclophosphamide, to destroy the leukemic cell population in locations other than the bone marrow or in sanctuaries within the bone marrow. In other instances in conjunction with the bone marrow suppression method of the present invention, it may be desirable to employ total body irradiation, with or without chemotherapeutic agents, as a treatment used to reduce the leukemic cell population, such as by delivering radiation to the patient from dual opposing cobalt-60 sources.

The general techniques of bone marrow transplantation are well known in the art, see for example, F. R. Appelbaum et al., "The Role of Marrow Transplantation in the Treatment of Leukemia", (pp. 229-262), C. D. Bloomfield (ed.), *Chronic and Acute Leukemias in Adults*, 1985, Martinus Nijhoff Publishers, Boston: E. D. Thomas, "Clinical Trials with Bone Marrow Transplantation", (pp. 239-253), *Clinical Trials in Cancer Medicine*, 1985, Academic Press, Inc.: E. D. Thomas, "Marrow Transplantation for Malignant Diseases", (pp. 517-531), *Journal of Clinical Oncology*, Vol. 1, No. 9 (September) 1983: E. D. Thomas et al., "Marrow Transplantation for Thalassemia", (pp. 417-427), *Annals New York Academy of Sciences*, 445, 1985. Under general or spinal anesthesia and using standard marrow aspiration needles, multiple aspirates are performed from the anterior and posterior iliac crests and, occasionally, the sternum of the donor. The marrow is placed in heparinized tissue culture media and then, using metal screens, filtered to remove bony spicules and fat globules and to create a monocellular suspension. At the time of desired administration of the bone marrow, the marrow is infused intravenously, following which the marrow stem cells migrate to the marrow space, proliferate, and eventually restore normal hematopoiesis and immune function. It is probably important to give as many bone marrow cells as possible to enhance the prospects of marrow engraftment. Following the transplant the patient usually receives some form of immunosuppression such as by being administered methotrexate or cyclosporine, in an attempt to prevent or at least modify graft-versus-host disease.

The following examples are included to aid in the understanding of the invention but are not to be construed as limiting the invention.

EXAMPLE A (COMPARATIVE)

Preparation of ethylenediaminetetramethylenephosphonic acid (EDTMP).

Into a suitable reaction vessel equipped with a thermometer, magnetic stirring bar, dropping funnel, and an atmosphere of nitrogen was charged 94.5 grams (g) of phosphorous acid and 100 milliliters (mL) of degassed water. Dissolution of the phosphorous acid was achieved by stirring and then 112 mL of concentrated hydrochloric acid was added. The dropping funnel was charged with 15 g of ethylenediamine and adjusted to allow dropwise addition of the ethylenediamine to the acidic solution. When addition was completed, the solution was refluxed for one hour using a heating mantle. At the end of the one hour reflux period, the dropping funnel was charged with 85 g (37 percent (%) aqueous solution) of formaldehyde which was added dropwise over a two hour period with continued heating to maintain reflux during the addition. After all of the formaldehyde was added, the reaction mixture was stirred under reflux for an additional two hours, then allowed to cool slowly overnight during which time the product precipitates. Vacuum filtration followed by cold water washing gives ethylenediaminetetramethylenephosphonic acid (EDTMP).

EXAMPLE 1

Preparation of 1,4,7,10-tetraazacyclododecanetetramethylenephosphonic acid (DOTMP).

In a 100-mL three necked round-bottomed flask equipped with a thermometer, reflux condenser, and heating mantle was added 3.48 g (20.2 mmole) of 1,4,7,10-tetraazacyclododecane and 14 mL of water. This solution was treated with 17.2 mL of concentrated HCl and 7.2 g of $H_3PO_3$ (87.8 mmole) and heated to 105° C. The refluxing suspension was stirred vigorously and treated dropwise with 13 g (160.2 mmole) of formaldehyde (37 wt % in water) over a one hour period. At the end of this time the reaction was heated at reflux an additional 2 hours, after which the heat was removed and the reaction solution allowed to cool and set at room temperature (about 20°-30° C.) for 62.5 hours. The reaction solution was then concentrated inin vacuo at 40° C. to a viscous reddish brown semisolid. A 30 mL portion of water was added to the semisolid which started to dissolve but then began to solidify. The whole suspension was then poured into 400 mL of acetone with vigorously stirring. The resulting off-white precipitate was vacuum filtered and dried overnight to give 10.69 g (97% yield) of crude DOTMP. A 2.0 g (3.65 mmole) sample of the crude DOTMP was dissolved in 2 mL of water by the addition of 700 μL of concentrated ammonium hydroxide (10.0 mmole) in 100 μL portions to give a solution at pH=2-3. This solution was then added all at once to 4.5 mL of 3 N HCl (13.5 mmole), mixed well, and allowed to set. Within one hour small squarish crystals had begun to form on the sides of the glass below the surface of the liquid. The crystal growth was allowed to continue undisturbed for an additional 111 hours after which time the crystals were gently bumped off of the vessel walls, filtered, washed with four 3-mL portions of water, and air dried to constant weight to give 1.19 g (60% yield) of white crystalline solid DOTMP.

EXAMPLE 2

A 250 mL three-necked, round-bottomed flask was loaded with 6.96 g (0.04 moles) of 1,4,7,10-tetraazacyclododecane. To this flask was added 14.5 g (0.177 moles) of phosphorous acid, 30 mL of deionized water and 28 mL of concentrated hydrochloric acid (0.336 moles).

The flask was attached to a reflux condenser and fitted with a stir bar, and a thermometer adapted with a thermowatch controller. A separate solution of 26.0 g (0.32 moles) of aqueous 37% formaldehyde solution was added to a 100 mL addition funnel and attached to the flask. The flask was brought to reflux temperature (about 105° C.) with vigorous stirring. The formaldehyde solution was added dropwise over a 30–40 minute interval. The solution was heated and stirred for an additional three hours then cooled slowly to ambient temperature.

The reaction solution was transferred to a 500 mL round-bottomed flask and attached to a rotary evaporation apparatus. The solution was taken down to a viscous, amber semi-solid (note-temperature never exceeded 40° C.). This semi-solid was treated with approximately 300 mL of HPLC grade acetone producing a light brown, sticky viscous oil. This oil was dissolved in 22 mL of water and added slowly with vigorous stirring to 1 L of acetone. The acetone was decanted and the light colored oil dried under vacuum to give 16.6 g (76% yield) of crude DOTMP. To 13.1 g of this crude DOTMP was added 39.3 g of deionized water along with a seed crystal and the solution allowed to stand overnight. The resulting precipitate was vacuum filtered, washed with cold water, and dried under vacuum to give 4.75 g of DOTMP (36% yield).

A further purification was performed by dissolving 3.0 g (5.47 mmole) of DOTMP from above in 3 mL of water by the addition of 2.2 mL (31.5 mmole) of concentrated ammonium hydroxide. This solution was made acidic by the addition of 2.4 mL (28.8 mmole) of concentrated HCl at which time a white solid precipitated. This precipitate was vacuum filtered and dried to give 2.42 g (81% yield) of purified DOTMP characterized by a singlet at 11.5 ppm (relative to 85% $H_3PO_4$) in the $^{31}P$ decoupled NMR spectrum.

EXAMPLE 3

Preparation of 153Sm solution.

Sm-153 can be produced in a reactor such as the University of Missouri Research Reactor. Sm-153 is produced by irradiating 99.06 percent enriched $^{152}Sm_2O_3$ in the first row reflector at a neutron flux of $8 \times 10^{13}$ neutron/cm$^2$·sec. Irradiations were generally carried out for 50 to 60 hours, yielding a Sm-153 specific activity of 1000–1300 Ci/g.

To irradiate $Sm_2O_3$ for production of Sm-153, the desired amount of target is first weighed into a quartz vial, the vial flame sealed under vacuum and welded into an aluminum can. The can is irradiated for the desired length of time, cooled for several hours and opened remotely in a hot cell. The quartz vial is removed and transferred to a glove box, opened into a glass vial which is then sealed. An appropriate amount of a solution of hydrochloric acid is then added to the vial via syringe in order to dissolve the $Sm_2O_3$. Once the $Sm_2O_3$ is dissolved, the samarium solution is diluted to the appropriate volume by addition of water. The solution is removed from the original dissolution vial which contains the chards of the quartz irradiation vial, and transferred via syringe to a clean glass serum vial.

EXAMPLE 4

Preparation of $^{166}$Ho solution.

Holmium-166 is prepared by weighing 0.5-1.0 mg of $Ho_2O_3$ into a quartz vial. The vial is sealed and placed in an aluminum can which is welded shut. The sample is irradiated (usually for about 24-72 hours) in a reactor (first row reflector, neutron flux of $8 \times 10^{13}$ neutron/cm$^2$·sec). After irradiation, the vial is opened and the oxide is dissolved using 4 Normal (N) HCl. Heating may be necessary. Water is then used to dilute the sample to an appropriate volume.

Preparation of $^{159}$Gd solution.

Gadolinium-159 is prepared by sealing gadolinium oxide (1.1 mg) in a quartz vial. The vial is welded inside an aluminum can and irradiated for 30 hours in a reactor at a neutron flux of $8 \times 10^{13}$ neutron/cm$^2$·sec. The contents of the quartz vial is dissolved using HCl. Water is added to obtain a solution of Gd-159 in 0.1 N HCl.

EXAMPLE 6

Preparation of $^{90}$Y solution.

A commercially available Yttrium-90 solution (Oak Ridge National Laboratories, Oak Ridge, Tenn.) was received as 100 mCi/0.53 mL no carrier added solution of Y-90 as the trichloride in 0.1 N HCl. A nonradioactive YCl$_3$ solution (0.0003 M) in 0.1 N HCl was prepared. A 700 μL ($2.1 \times 10^{-7}$ mol) portion of the nonradioactive YCl$_3$ solution was added to 45 μL of Y-90 solution to give a final YCl$_3$ solution at $2.82 \times 10^{-4}$ M containing Y-90.

EXAMPLE B (COMPARATIVE)

Preparation of $^{153}$Sm-EDTMP.

A solution of 0.3 mM Sm in 0.1 N HCl was spiked with Sm-153. Three mL of this solution was transferred to a vial containing a freeze dried solution of NaOH and ethylenediaminetetramethylenephosphonic acid (EDTMP). The resultant concentration of EDTMP was 35 mg/mL and the pH was between 7 and 8. Lower ligand to metal ratios were obtained by diluting the stock Sm-EDTMP solution with Sm solution and adjusting the pH to 7-8. The amount of metal found as a complex was determined by cation exchange chromatography to be >99% for all the solutions.

Sprague Dawley rats were allowed to acclimate for five days then injected with 100 μL of the Sm-EDTMP solutions via a tail vein. The rats weighed between 150 and 200 g at the time of injection. After 2 hours the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ. The percent of the injected dose in liver for formulations at various EDTMP to Sm molar ratios are given in Table I. The numbers represent the average of 3 rats per data point.

TABLE I

| % INJECTED DOSE IN LIVER AT VARIOUS EDTMP TO Sm RATIOS | | |
|---|---|---|
| EDTMP[1] | L:M[2] | % Dose in Liver |
| 0.002 | 8 | 1.8 |
| 0.006 | 19 | 0.64 |
| 0.011 | 38 | 0.33 |
| 0.023 | 76 | 0.17 |
| 0.046 | 153 | 0.15 |

[1]EDTMP is in moles per liter.
[2]L:M = The ligand to Sm molar ratios

EXAMPLE C (COMPARATIVE)

Preparation of $^{166}$Ho-EDTMP.

A solution of 0.6 mM Ho in 0.1 N HCl was spiked with Ho-166. Three mL of this solution was transferred to a vial containing a freeze dried solution of NaOH and ethylenediaminetetramethylenephosphonic acid (EDTMP). The resultant concentration of EDTMP was 35 mg/mL and the pH was between 7 and 8. Lower ligand to metal ratios were obtained by diluting the stock Ho-EDTMP solution with Ho solution and adjusting the pH to 7-8. The amount of metal found as a complex was determined by cation exchange chromatography to be >99% for all the solutions.

Sprague Dawley rats were allowed to acclimate for five days then injected with 100 μL of the Ho-EDTMP solutions via a tail vein. The rats weighed between 150 and 200 g at the time of injection. After 2 hours the rats were killed by cervical dislocation and dissected. The amount of radioactivity in each tissue was determined by counting in a NaI scintillation counter coupled to a multichannel analyzer. The counts were compared to the counts in 100 μL standards in order to determined the percentage of the dose in each tissue or organ. The percent of the injected dose in liver for formulations at various EDTMP to Ho molar ratios are given in Table II. The numbers represent the average of 5 rats per data point.

TABLE II

| % INJECTED DOSE IN LIVER AT VARIOUS EDTMP TO Ho RATIOS | | |
|---|---|---|
| EDTMP[1] | L:M[2] | % Dose in Liver |
| 0.042 | 70 | 0.07 |
| 0.030 | 50 | 0.08 |
| 0.024 | 39 | 0.07 |
| 0.018 | 30 | 0.10 |
| 0.012 | 20 | 0.17 |
| 0.006 | 10 | 0.79 |
| 0.003 | 5 | 0.94 |

[1]EDTMP is in moles/liter.
[2]L:M = ligand to Ho molar ratio

EXAMPLE 7

Preparation of $^{153}$Sm-DOTMP

The ligand of Example 1 (22 mg) was dissolved in 878 μL of distilled water and 15 μL of 50% NaOH. A volume of 15 μL of this solution was transferred to a vial containing 1.5 mL of Sm solution (0.3 mM Sm in 0.1 N HCl spiked with 2 μL of Sm-153 tracer). The pH was adjusted to 7-8 using NaOH and the amount of Sm found as a complex was greater than 99% as determined by ion exchange chromatography. This yielded a solution containing Sm at 0.3 mM with a ligand to metal molar ratio of approximately 1.5.

Sprague Dawley rats were allowed to acclimate for five days then injected with 100 μL of the Sm solution described above via a tail vein. The rats weighed between 150 and 200 g at the time of injection. After 2 hours the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ. The percent of the injected dose in several tissues are given in Table III. The numbers represent the average of 3 rats per data point.

TABLE III

| % INJECTED DOSE IN SEVERAL TISSUES FOR Sm-DOTMP[1] | |
|---|---|
| Bone | 58.1 |
| Liver | 0.06 |
| Kidney | 0.27 |
| Spleen | 0.004 |
| Muscle | 0.15 |
| Blood | 0.004 |

[1]Ligand to Sm Molar Ratio of approximately 1.5

EXAMPLE 8

Preparation of [166]Ho-DOTMP.

The ligand of Example 1 (22 mg) was dissolved in 878 μL of distilled water and 15 μL of 50% NaOH. A volume of 30 μL of this solution was transferred to a vial containing 1.5 mL of Ho solution (0.6 mM Ho in 0.1 N HCl spiked with 2 μL of Ho-166 tracer). The pH was adjusted to 7-8 using NaOH and the amount of Ho found as a complex was greater than 99% as determined by ion exchange chromatography. This yielded a solution containing 0.6 mM Ho with a ligand to metal molar ratio of approximately 1.5.

Sprague Dawley rats were allowed to acclimate for five days then injected with 100 μL of the Ho solution described above via a tail vein. The rats weighed between 150 and 200 g at the time of injection. After 2 hours the rats were killed by cervical dislocation and dissected. The amount of radioactivity in each tissue wa determined by counting in a NaI scintillation counter coupled to a multichannel analyzer. The counts were compared to the counts in 100 μL standards in order to determine the percentage of the dose in each tissue or organ. The percent of the injected dose in several tissues are given in Table IV. The numbers represent the average of 3 rats per data point.

TABLE IV

| % INJECTION DOSE IN SEVERAL TISSUES FOR Ho-DOTMP[1] | |
|---|---|
| Bone | 57 |
| Liver | 0.07 |
| Kidney | 0.4 |
| Spleen | 0.006 |
| Muscle | 0.3 |
| Blood | 0.07 |

[1]Ligand to Ho Molar Ratio of approximately 1.5

EXAMPLE 9

Preparation of [153]Sm-DOTMP and [166]Ho-DOTMP.

A quantity of 14.5 mg of the ligand of Example 2 was placed in a vial and dissolved in 760 μL of water and 5 μL of 50% NaOH. A volume of 1100 μL of Sm solution (0.3 mM Sm in 0.1 N HCl) which was spiked with Sm-153, was placed in a separate vial and 10 μL of the ligand solution was added. The pH of the solution was adjusted to 7-8 using NaOH and the solution was passed through 3 plastic columns containing 1.5 mL of cation exchange resin (Sephadex C-25 from Pharmacia). The amount of Sm as a complex was determined to be 99% by cation exchange chromatography.

A volume of 1100 μL of Ho solution (0.6 mM Ho in 0.1 N HCl) which was spiked with Ho-166, was placed in a separate vial and 20 μL of the above ligand solution was
added. The pH of the solution was adjusted to 7-8 using NaOH and the solution was passed through 2 plastic columns containing 1.5 mL of cation exchange resin (Sephadex C-25 from Pharmacia). The amount of Ho as a complex was determined to be 99% by cation exchange chromatography.

Sprague Dawley rats were allowed to acclimate for five days then injected with 100 μL of the solutions described above via a tail vein. The rats weighed between 150 and 200 g at the time of injection. After 2 hours the rats were killed by cervical dislocation. Tissues were taken, weighed and the amount of radioactivity determined by counting in a NaI scintillation counter coupled to a multichannel analyzer. The counts in each tissue were compared to the counts in 100 μL standards in order to determine the percentage of the dose in each tissue or organ. The percent of the injected dose in several tissues are given in Table V. The numbers represent the average of 3 rats per data point.

TABLE V

| % INJECTED DOSE IN SEVERAL TISSUES FOR DOTMP METAL COMPLEXES | | |
|---|---|---|
|  | Sm | Ho |
| Bone | 50 | 64 |
| Liver | 0.37 | 0.19 |
| Kidney | 0.29 | 0.32 |
| Spleen | 0.04 | 0.05 |
| Muscle | 0.49 | 0.22 |
| Blood | 0.12 | 0.17 |

EXAMPLE 10

Preparation of [166]Ho-DOTMP.

A volume of 0.5 mL of non-radioactive holmium solution (0.6 mM) in 0.1 N HCl was mixed with 0.5 mL of Ho-166 solution (also 0.6 mM in Ho, dissolved in 0.1 N HCl) in a plastic vial. To this was added 30 μL of a 33 mM aqueous solution of the ligand of Example 2. Sodium hydroxide (50%) was added slowly until the pH was between 7 and 8. The percentage of the total Ho found as a complex was determined to be greater than 99% by cation exchange chromatography.

Six Sprague Dawley rats were allowed to acclimate for a period of 6 days then a sample of blood was taken daily from the tail vein and the white blood cell count determined by a standard manual method (Unopette Test 5856 from Becton-Dickinson and Company). On the fourth day, rats numbered 2, 4 and 6 were injected with 0.9 mCi (33.3 MBq) of the above complex. The rat weight at this time ranged from 160-180 g. On days 7, 8, and 9 the white blood cell count was again determined for each rat. Table VI gives the white blood cell count of the injected (2, 4 and 6) rats compared to the control rats (1, 3, and 5). There is a significant drop in the blood count of the treated animals compared to the untreated animals.

TABLE VI

| Rat[1] | WHITE BLOOD CELL COUNTS | | | | | | |
| --- | --- | --- | --- | --- | --- | --- | --- |
| | Day 1 | Day 2 | Day 3 | Day 4* | Day 7 | Day 8 | Day 9 |
| 1 | 17650 | 16500 | 18550 | 19950 | 20550 | 19750 | 21500 |
| 2 | 16550 | 15850 | 19900 | 28950 | 5850 | 7950 | 7900 |
| 3 | 21650 | 19250 | 20300 | 20550 | 22700 | 26550 | 26050 |
| 4 | 20900 | 20300 | 21500 | 21300 | 7400 | 7500 | 7550 |
| 5 | 20650 | 19400 | 20250 | 20950 | 18700 | 17700 | 23750 |
| 6 | 20250 | 18400 | 17450 | 17600 | 5400 | 4750 | 5350 |

*Date of injection
[1]Rats 1, 3 and 5 are control; Rats 2, 4 and 6 were injected with Ho-DOTMP.

EXAMPLE 11

Preparation of $^{159}$Gd-DOTMP.

The ligand of Example 2 (14.5 mg) was placed in a vial and dissolved in 760 μL of water and 5 μL of 50% NaOH. A volume of 1000 μL of Gd solution (0.3 mM Gd in 0.1 N HCl) which contained tracer quantities of Gd-159, was placed in a separate vial and 15 μL of the ligand solution was added. The pH of the solution was adjusted to 7-8 using NaOH and the amount of Gd as a complex was determined to be )99% by cation exchange chromatography.

A Sprague Dawley rat was allowed to acclimate for five days then injected with 175 μL of the solution described above via a tail vein. The rat weighed 155 g at the time of injection. After 2 hours the rat was killed by cervical dislocation and dissected. The amount of radioactivity in each tissue was determined by counting in a NaI scintillation counter coupled to a multichannel analyzer. The counts in each tissue were compared to the counts in 175 L standards in order to determine the percentage of the dose in each tissue or organ. The percent of the injected dose in several tissues are given in Table VII.

TABLE VII

| % INJECTED DOSE IN SEVERAL TISSUES FOR Gd-DOTMP | |
| --- | --- |
| Tissue | % Dose |
| Bone | 50 |
| Liver | 0.08 |
| Kidney | 0.25 |
| Spleen | None detected* |
| Muscle | 0.08 |
| Blood | 0.06 |

*Counts in the spleen were below background

Preparation of $^{90}$Y-DOTMP.

A 0.0015 M solution of the ligand of Example 2 was prepared and a 22.5 μL (3.3×10$^{-8}$ mol) portion was added to 745 μL (2.1×10$^{-7}$ mol) of Y-90 solution from Example 6. Sodium hydroxide (50%) was added slowly until the pH was 7.5. A 10.0 μL addition of the 100 mCi/0.53 mL no carrier added solution of Y-90 (described in Example 6) was then added to bring the specific activity to 1.0 mCi/100 μL. The percentage of the total Y found as a complex was determined to be greater than 99% by cation exchange chromatography.

Six Sprague Dawley rats were allowed to acclimate for a period of 6 days then a sample of blood was taken from the tail vein (day=−7) and the white blood cell count determined by a standard manual method (Unopette Test 5856 from Becton-Dickinson and Company). Three days later (day=−4) this procedure was repeated. Four days later (day=0) the procedure was again performed and rats 3, 5 and 6 were injected in the tail vein with 100 μL of the above $^{90}$Y-DOTMP complex. These injections contained approximately 1 mCi (37.0 MBq) of the above Y-90 complex each. On days 3 and 5 the white blood cell count was again determined for all 6 rats. Table VIII gives the white blood cell count of the injected (3, 5 and 6) rats compared to the control rats (1, 2 and 4). There is a significant drop in the blood count of the treated animals compared to the untreated animals.

TABLE VIII

| Rat[1] | WHITE BLOOD CELL COUNTS | | | | |
| --- | --- | --- | --- | --- | --- |
| | Day-7 | Day-4 | Day 0* | Day 3 | Day 5 |
| 1 | 13600 | 19200 | 16100 | 15000 | 19200 |
| 2 | 23000 | 20800 | 15400 | 19200 | 28400 |
| 3 | 21800 | 15000 | 16400 | 4000 | 2500 |
| 4 | 21600 | 22200 | 16800 | 18600 | 18600 |
| 5 | 14000 | 20800 | 13000 | 6250 | 3400 |
| 6 | 15600 | 18000 | 13650 | 5550 | 4200 |

*Date of injection
[1]Rats 1, 2 and 4 are control; Rats 3, 5 and 6 were injected with Y-DOTMP.

We claim:

1. A method for suppressing bone marrow which comprises administering to a mammal in need of such treatment a bone marrow suppressing amount of a bone marrow suppressing composition comprising the radionuclide Yttrium-90 complexed with at least one macrocyclic aminophosphonic acid ligand containing a 1,4,7,10-tetraazacylododecane moiety and wherein the phosphonic acid functionality is attached to the nitrogen of the macrocyclic polyamine through an alkylene group or a physiologically acceptable salt thereof.

2. The method of claim 1 wherein the ligand is 1,4,7,10-tetraazacyclododecanetetrmethylenephosphonic acid or a physiologically acceptable salt thereof.

3. The method of claim 1 used in conjunction with an additional treatment regimen using at least one of (a) one or more bone marrow suppressing agents, and/or (b) one or more chemotherapeutic agents, and/or (c) one or more radiotherapeutic agents or radiotherapeutic methods.

4. The method of claim 1 used in conjunction with total body irradiation or targeted external irradiation.

5. The method of claim 1 including the additional step of bone marrow transplantation after sufficient bone marrow suppression is achieved.

6. The method of claim 1 used in conjunction with a treatment employing at least one chemotherapeutic agent.

7. The method of claim 6 wherein the chemotherapeutic agent is selected from dimethyl busulfan, cyclophosphamide, bischloroethyl nitrosourea, cytosine arabinoside, and 6-thioguanine.

8. The method of claim 1 used in conjunction with total body irradiation and with a treatment employing at least one chemotherapeutic agent.

9. The method of claim 8 wherein the chemotherapeutic agent is selected from dimethyl busulfan, cyclophosphamide, bischloroethyl nitrosourea, cytosine arabinoside, and 6-thioguanine.

10. The method of claim 1 used in conjunction with one or more therapeutic regimens for the treatment of leukemia, lymphoma, myeloma or Hodgkin's disease.

11. The method of claim 10 wherein the disease being treated is a leukemia.

12. The method of claim 10 wherein the disease being treated is a lymphoma.

13. The method of claim 10 wherein the disease being treated is a myeloma.

14. The method of claim 10 wherein the disease being treated is Hodgkin's disease.

15. A sterile composition suitable for administration to a mammal for suppressing bone marrow comprising the radionuclide Yttrium-90 complexed with at least one macrocycle aminophosphonic acid ligand containing the 1,4,7,10-tetraazacyclododecane moiety or a physiologically acceptable salt thereof, wherein the phosphorous of said ligand is attached to the amine nitrogen through an alkylene moiety and wherein the radionuclide in dosage form is present in an amount containing from about 18 to about 1850 megabecquerels per kilogram of body weight of said mammal.

16. The composition of claim 15 wherein the ligand to radionuclide ratio is from 1:1 to 2:1.

17. A pharmaceutical formulation comprising the composition of claim 15 in a pharmaceutically acceptable carrier.

18. The composition of claim 15 wherein the dosage form contains from about 185 to about 1850 mega-becquerels per kilogram of body weight of said mammal.

19. The composition of claim 18 wherein the macrocyclic ligand is 1,4,7,10-tetraazacylododecanetetramethylenephosphonic acid.

20. The composition of claim 15 wherein the macrocyclic ligand is 1,4,7,10-tetraazacyclododecanetetramethylenephosphonic acid.

21. A pharmaceutical formulation comprising the composition of claim 20 in a pharmaceutically acceptable carrier.

* * * * *

UNITED STATES PATENT AND TRADEMARK OFFICE
CERTIFICATE OF CORRECTION

PATENT NO. : 4,976,950
DATED : December 11, 1990
INVENTOR(S) : Jaime Simon, et al.

It is certified that error appears in the above-indentified patent and that said Letters Patent is hereby corrected as shown below:

Column 4, line 32, "84,876," should correctly appear as -- 284.876, --.

Column 4, line 33, "C-2,813D" should correctly appear as --32,813D --.

Column 4, line 53, "humans:" should correctly appear as -- humans; --.

Column 5, line 51, "important:" should correctly appear as -- important; --.

Column 6, line19, "treated:" should correctly appear as -- treated; --; line 33, "marrow:" should correctly appear as -- marrow; --; line 50, "Inc.:" should correctly appear as -- Inc.; --; line 53, "1983:" should correctly appear as -- 1983; --.

Column 7, line 55, "inin" should correctly appear as -- in --.

Column 11, line 44, "wa" should correctly appear as -- was --.

Column12, lines 13 and 14 should be joined and correctly appear as one paragraph.

Column 13, line 25, ")99%" should correctly appear as -- >99% --; Line 50 a heading of -- Example 12 -- should be added.

Signed and Sealed this

Third Day of August, 1993

Attest:

MICHAEL K. KIRK

*Attesting Officer*    *Acting Commissioner of Patents and Trademarks*